United States Patent [19]

Hunnell et al.

[11] Patent Number: 5,082,254

[45] Date of Patent: Jan. 21, 1992

[54] MICROTOME OBJECT HOLDER ASSEMBLY

[75] Inventors: Jack E. Hunnell, Durham; John E. Hunnell, Raleigh; Thomas F. Jackson, Durham, all of N.C.

[73] Assignee: Triangle Biomedical Sciences, Inc., Durham, N.C.

[21] Appl. No.: 409,459

[22] Filed: Sep. 19, 1989
(Under 37 CFR 1.47)

[51] Int. Cl.$^5$ .............................................. B25B 1/24
[52] U.S. Cl. .................................. 269/269; 269/909
[58] Field of Search ............... 269/309, 269, 270, 253, 269/157, 160, 329, 909

[56] References Cited

U.S. PATENT DOCUMENTS

| | | | |
|---|---|---|---|
| 2,616,320 | 11/1952 | Vosper | 269/269 |
| 2,698,550 | 1/1955 | Hill | 269/270 |
| 4,390,172 | 6/1983 | Gotman | 269/309 |
| 4,610,020 | 9/1986 | La Fiandra | 269/309 |

Primary Examiner—Robert C. Watson
Attorney, Agent, or Firm—Olive & Olive

[57] ABSTRACT

A microtome object holder clamping assembly is disclosed, having utility for positioning a ball-mounted specimen plate in a spatially fixed manner, but which is selectively repositionable by pivotal and/or rotational movement to dispose the specimen plate at any desired orientation relative to the microtome knife element. The object holder clamping assembly comprises first and second clamping members, one of which has a generally V-shaped, conical spherical contoured channel therein which is disposable in proximity to a spherically contoured cavity in a second clamping member, whereby the ball of the ball-mounted specimen plate may be clamped in a three-point contacting arrangement. The microtome object holder clamping assembly of the invention may be usefully employed in a variety of microtome structures, including microtome cryostats, for sectioning of selected specimens.

15 Claims, 6 Drawing Sheets

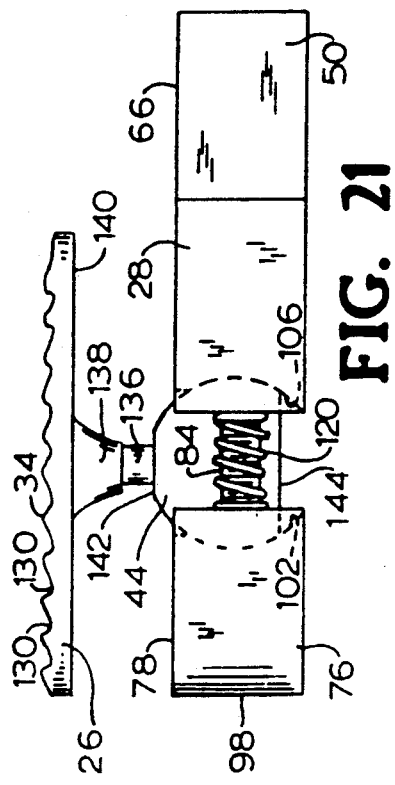
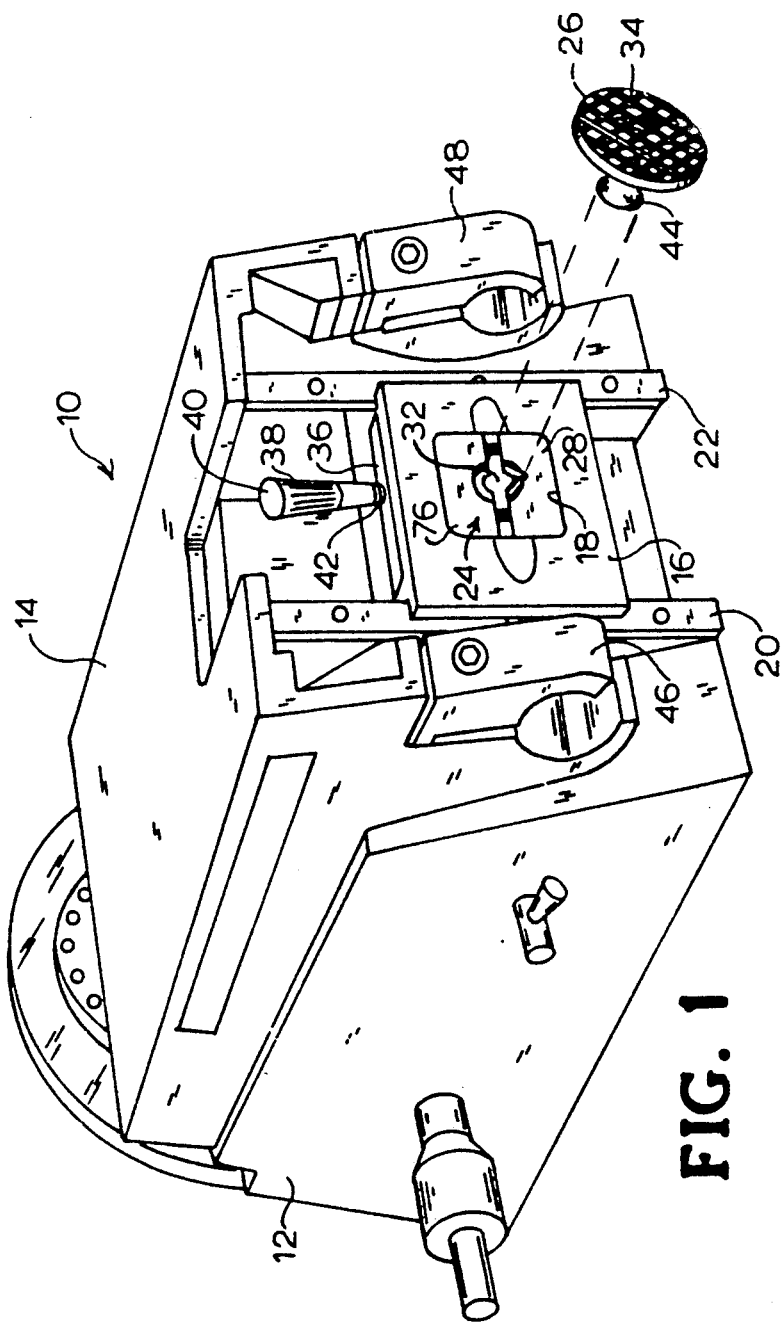
FIG. 21
FIG. 1

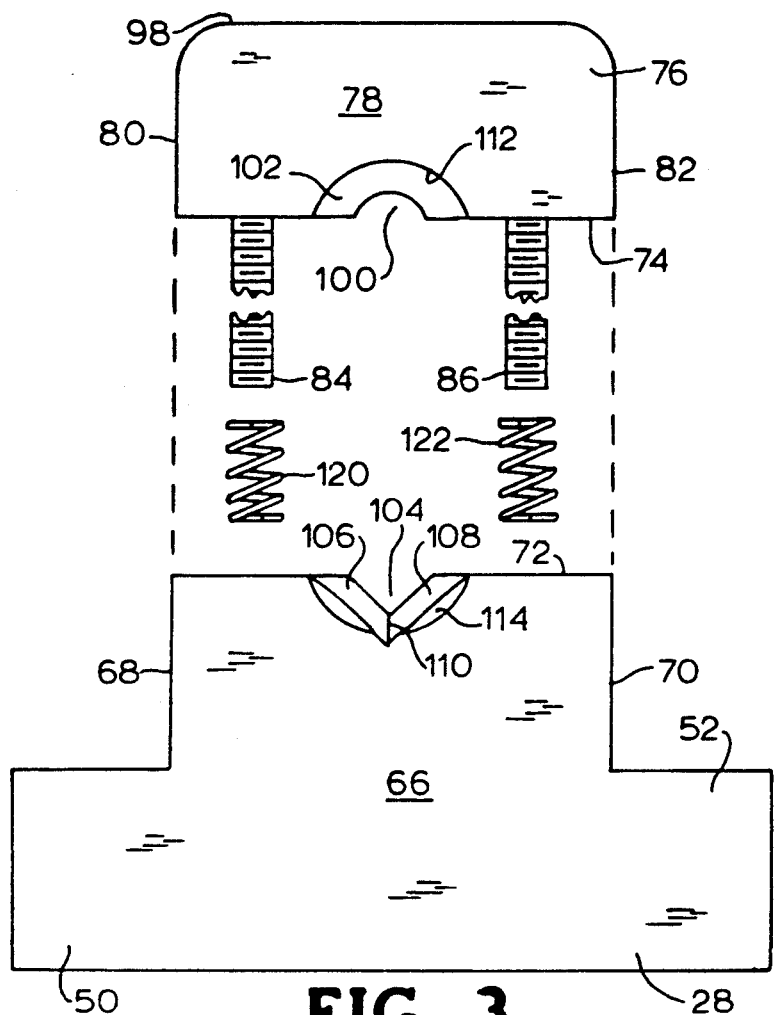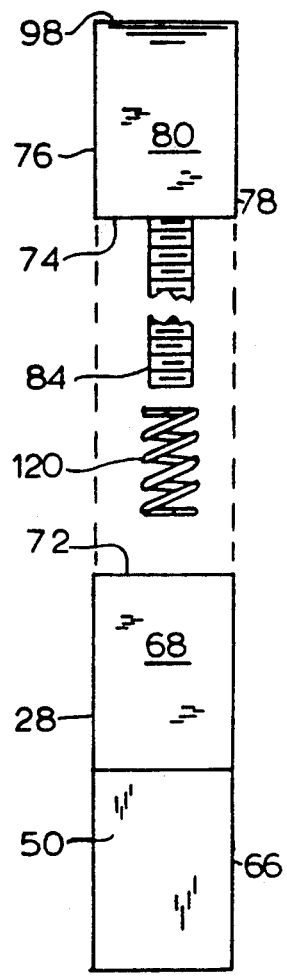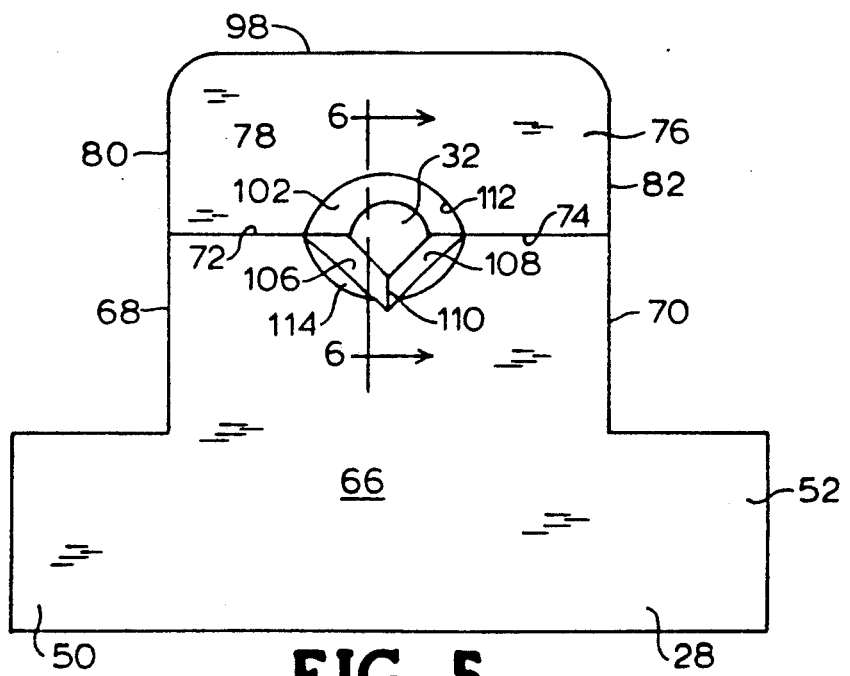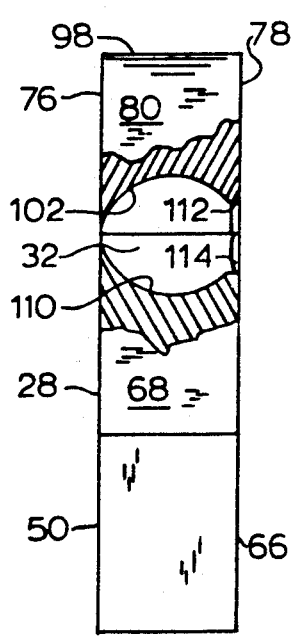
FIG. 3
FIG. 4
FIG. 5
FIG. 6

MICROTOME OBJECT HOLDER ASSEMBLY

BACKGROUND OF THE INVENTION

1. Field of Invention

This invention relates to a microtome object holder clamping structure for a ball-mounted specimen plate, and to a microtome object holder assembly comprising such structure.

2. Description of the Related Art

For histological analysis of samples and determination of their physiological and pathology characteristics, microtomes are utilized to produce extremely thin sections of a selected tissue specimen for microscopic examination.

For such sectioning, the microtome typically employs a specimen plate as a substrate element to which the tissue sample is affixed by an adhesive embedding medium. The specimen plate bearing such tissue sample then is clamped or otherwise fixedly positioned in the microtome apparatus, in proximity to a knife which is translatable into cutting contact with the mounted specimen, to yield thin cut sections of tissue for analysis.

In some instances, it is desirable to cryogenically fix the biological specimen by cooling it to low temperatures on the order of $-100°$ C. to about $-190°$ C. to produce a frozen "vitrified" sample for sectioning and analysis. Accordingly, cryostat microtomes have come into usage in which the microtome unit is mounted in a cooling enclosure. In such apparatus, the microtome is coupled to externally mounted controls to actuate and control the microtome. An illustrative cryostat microtome of such type is disclosed in U.S. Pat. No. 4,548,051 issued Oct. 22, 1985 to G. Moessner.

In recent years cryostat microtomes have become increasingly sophisticated, utilizing digital controls and monitoring devices affording a highly accurate, low-distortion sectioning operation. As an example, the Minotome ® Digital Microtome-Cryostat, a cryostat microtome unit commercially available from International Equipment Company (Needham Heights, MA), is said to permit cutting of tissue sections with a thickness of from 2 to 42 microns, in precise 2 micron increments.

With such precision sectioning ability, it is critically important in the operation of the microtome that the mounted specimen be retained in a spatially fixed position, since any movement of the specimen relative to the precision controlled cutting blade will produce sections of uneven thickness. Such variability in turn introduces a distortion and possible error into the subsequent microscopic analysis of the tissue, and may lead to mis-characterization or mis-diagnosis of the tissue, or else require discarding of the sample and repetition of the sectioning effort.

In this respect, the bearing pressure exerted by the microtome knife on the sample is significant, particularly in the case of the aforementioned cryogenically frozen samples, which present a high cutting resistance relative to ambient temperature specimens. Thus, the shear, bearing, and torsional stresses variously exerted by the knife on the specimen may tend to cause the specimen plate to shift in its mounting structure, with the above-described adverse affects on uniform sectioning ability. It is therefore necessary that the specimen holder be mounted in a manner so that it resists any movement in the presence of such stresses.

At the same time, it is highly desirable, and in some instances critical, to provide the specimen plate with the ability to be selectively adjusted in position, so that the orientation of the microtome knife relative to the specimen mounted on the holder may be correspondingly varied.

These features—the requirement that the specimen plate be fixedly positioned and positionally constant during the sectioning operation, and the capability of the specimen holder to be selectively repositioned for subsequent sectioning operations—are frequently at odds with one another in the specimen plate assemblies which have been devised to date. In such systems, the adjustability of the specimen plate's position is accommodated by specimen plate mounting units which frequently are susceptible to slippage and movement as a result of the sectioning operation, so that it is difficult to maintain a desired uniformity of thickness of tissue specimens, particularly when the number of successive sections to be cut from the sample is large.

As an example of the foregoing difficulties, a widely employed microtome assembly is the International Minot Custom Microtome, commercially available from International Equipment Company (Needham Hights, MA), which features a specimen plate to which is threadably attached, on the side opposite the specimen mounting face of the plate, a ball and stem fitting. After attachment of the specimen plate to the ball and stem unit, the ball is introduced into a clamp device featuring an opening communicating with a generally spherical interior cavity. The ball of the specimen mounting assembly is inserted into this cavity. A set screw then is threadably advanced into the cavity so that its end surface bears compressively against the ball. This type of arrangement produces a "two point contact" of the ball, with one contact point being between the planar end surface of the set screw and the ball, and the other contact point being diametrally opposite the first contact point, where the ball bears against the interior surface of the receiving cavity. As a result of this two contact point arrangement, the specimen holder is susceptible to rotational movement about the contact points, as well as slippage caused by the forces exerted on the specimen during the cutting operation. Further, any low level vibration, movement, or adjustment of the microtome unit may cause the set screw to loosen and the ball to shift, along with the specimen plate and the specimen thereon.

Microtome specimen holder assemblies also have been utilized which feature a ball-mounted specimen plate held in fixed position by three opposedly arranged set screws. In such arrangement, a circumferential spacing of 120° exists between the successive screws in the set screw array, so that a "three contact point" arrangement is provided when the respective set screws are threadably advanced into bearing contact with the ball element of the specimen holder. While this arrangement is effective to spatially fix the specimen, it has the attendant disadvantage that three set screws must be successively tightened to grip the ball. Manual repositioning of the specimen holder entails readjustment of these multiple screws, so that the positioning of this assembly is tedious and time-consuming in character.

Other set screw-type specimen plate or specimen holder mounting arrangements are shown in U.S. Pat. No. 2,155,523 issued Apr. 25, 1939 to E. Bausch et al and U.S. Pat. No. 3,091,144 issued May 28, 1963 to H. Fernandez-Moran Villalobos.

Alternative approaches which have been proposed include the magnetic mounting structure described in U.S. Pat. No. 3,190,164 issued June 22, 1965 to J. B. McCormick. In the system disclosed in that patent, the specimen is mounted on a magnetic chuck device, however such arrangement is subject to the same displacement and positional shifting disadvantages as the aforementioned mechanical mounting structures.

Accordingly, it would be a significant advance in the art to provide a specimen holder mounting structure which overcomes the above-described deficiencies.

It is therefore an object of the present invention to provide an improved microtome specimen holder mounting structure, which accommodates selective fixed positioning of a ball-mounted specimen plate in a manner which is highly resistant to movement during operation of the microtome, and which at the same time is readily selectively repositionable to different orientations.

It is another object of the present invention to provide a microtome specimen holder mounting structure of such type, which utilizes only a single adjustment element, and in which the ball-mounted specimen plate is readily adjustible, both rotationally and translationally, to a subsequently desired fixed position.

Other objects and advantages of the present invention will be more fully apparent from the ensuing disclosure and appended claims.

SUMMARY OF THE INVENTION

The present invention relates in one aspect to a microtome object holder clamping structure for a ball-mounted specimen plate. The clamping structure comprises first and second clamping members positionable in proximity to one another to define therebetween a retention cavity for the ball of the ball-mounted specimen plate. A portion of this cavity is defined by the first clamping member, which has a V-shaped channel therein extending from the front surface to the back surface of the clamping member. The side walls of the V-shaped channel have a conical spherical contour. The second clamping member has a channel therein which is complementary to the channel of the first clamping member, to define the aforementioned cavity therebetween. The channel in the second clamping member likewise extends from the front surface to the back surface of the clamping member, with the interior surface bounding the channel of such clamping member having a spherical contour.

This clamping structure further comprises a means for adjustably engaging the first and second clamping members in clamping relationship relative to one another, with a ball of a ball-mounted specimen plate disposed in the cavity defined by the clampingly positioned first and second clamping members, whereby a three point contact of the clamping members with the ball element of the specimen plate is obtained.

In another aspect, the present invention relates to a microtome comprising a specimen holder clamping structure of the type broadly described above.

Other objects and advantages will be more fully apparent from the ensuing disclosure and appended claims.

BRIEF DESCRIPTION OF THE DRAWINGS

FIG. 1 is a perspective view of a microtome according to one embodiment of the present invention, featuring a specimen holder clamping assembly in accordance with the present invention.

FIG. 3 is a front elevation view of the clamping members of the microtome specimen holder clamping assembly of FIG. 2, wherein the first and second clamping members are in exploded relationship to one another.

FIG. 4 is a side elevation view of the microtome specimen holder clamping assembly of FIG. 3.

FIG. 5 is a rear elevation view of the first and second clamping members of the microtome specimen holder clamping assembly of FIGS. 3-4, wherein the spacer springs 120 and 122 have been removed so that the clamping members abut one another.

FIG. 6 is a side elevation view of the microtome specimen holder clamping assembly of FIG. 5.

FIG. 21 is a side elevation view of the microtome specimen holder unit of FIG. 17.

DETAILED DESCRIPTION OF THE INVENTION, AND PREFERRED EMBODIMENTS THEREOF

Figure 2:
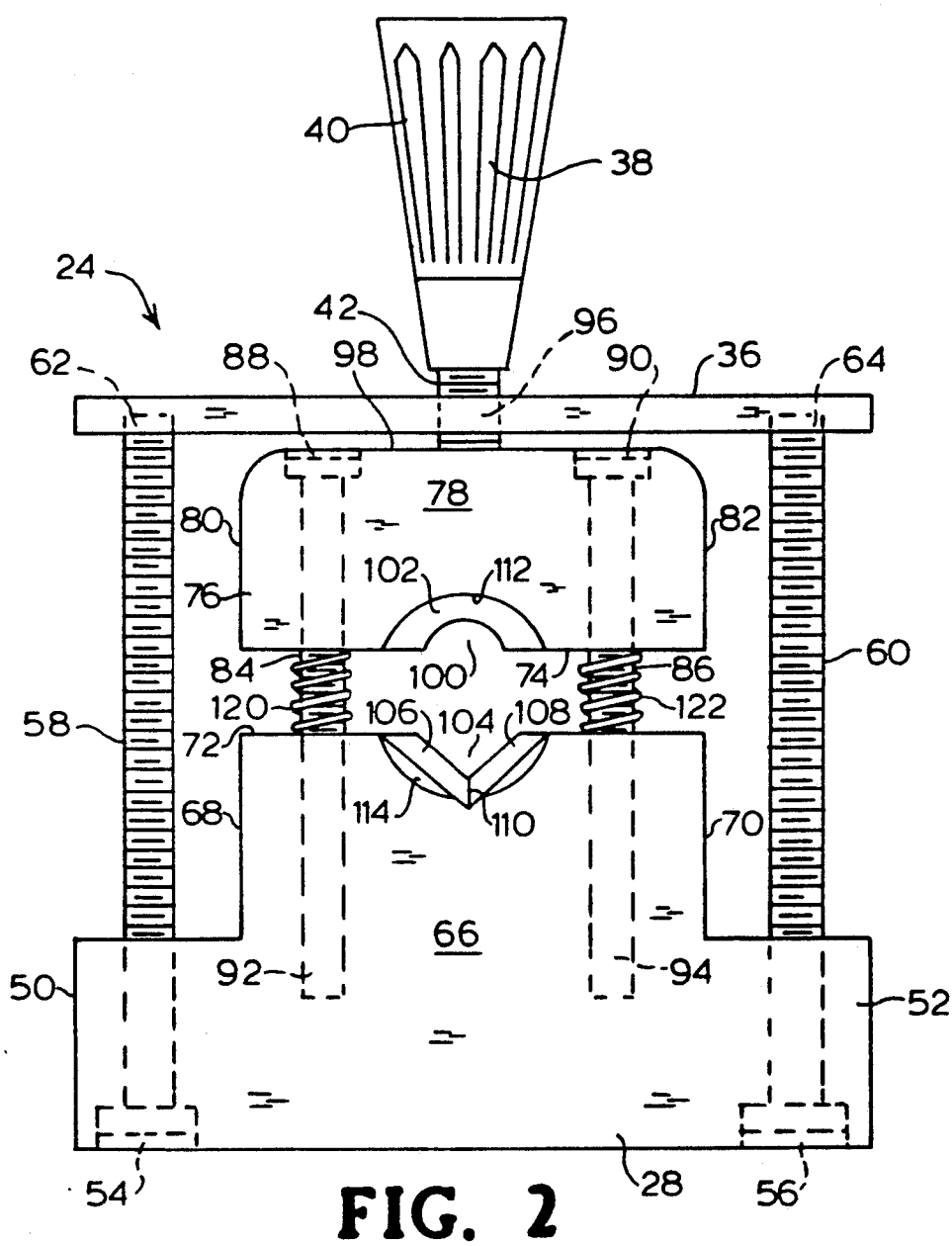
FIG. 2 is a front elevation view of the microtome specimen holder clamping assembly employed in the microtome of FIG. 1.

Referring now to the drawings, FIG. 1 shows a perspective view of a microtome according to one embodiment of the present invention.

The microtome 10 illustratively shown in this drawing is of a type as more fully described in U.S. Pat. No.

3,212,379 issued Oct. 19, 1965 to J. B. McCormick, et al, the disclosure of which hereby is incorporated herein by reference. Such microtome is commercially available as Microtome Model 4551 from the Ames Division of Miles Laboratory, Inc. (Elkhart, Ind.) and may suitably be mounted in a cryostat for sectioning of frozen specimens.

The microtome 10 comprises a walled housing 12 having a top wall 14 which is slidably moveable in a generally horizontal plane. On the front portion of the housing is provided an upstanding wall 16 with an elongated generally vertically disposed opening 18 and a pair of vertically disposed, horizontally spaced guides 20, 22 positioned adjacent the opening. An object holder clamping assembly 24 is positioned within the opening 18, which is constructed and arranged to retentively engage ball-mounted specimen plate 26, as hereinafter more fully desscribed.

The object holder clamping assembly comprises a first clamping member 28, and a second clamping member 76, which are selectively positionable in clamping relationship relative to one another. Each of these clamping members 28,76 is provided with a channel in its facing surface, so that upon being disposed in clamping relationship to one another as shown, a central cavity 32 is defined by the corresponding channels. In the microtome 10 as illustrated, the clamping assembly 24 is positioned for reciprocal sliding movement on the guides 20 and 22, so as to move the specimen bearing surface 34 of the specimen plate 26 in a generally vertical plane.

Mounted on the upper end of the upstanding wall 16 is a generally horizontal end plate 36, which in turn mounts an adjustment screw member 38 including a manually grippable handle portion 40 and a lower threaded portion 42. The function of the adjustment screw member 38 is to exert compression on first and second clamping members 28 and 76 when the ball 44 attached to specimen plate 26 is selectively reposed in cavity 32 and adjustment screw member 38 is tightened. Alternatively, when it is desired to remove the ball of the ball-mounted specimen plate 26 from cavity 32, the adjustment screw member 38 is selectively loosened so that the first and second clamping members may be disengaged from contact with the ball 44 attached to the specimen plate 26.

Although not shown for reasons of clarity, the microtome 10 as fully constituted includes a knife suspended from the top wall 14 of the housing, by means of the clamping arms 46 and 48, so that the knife is in adjacent relation to the specimen-bearing surface 34 of the object holder. Such knife includes a cutting edge disposed in generally parallel relation to the specimen mounting surface 34. Means are provided within the housing 12 for effecting reciprocal movement of the clamping assembly 24, and for effecting incremental sliding movement of the top wall 14 of the housing 12 incident to the reciprocal movement of the clamping assembly 24, such as will move the knife in the direction of the specimen-bearing surface 34.

As indicated, the structure and function of the microtome 10, with the exception of the object holder clamping assembly 24 and ball-mounted specimen plate 26, is set out in greater detail in the aforementioned U.S. Pat. No. 3,212,379.

FIG. 2 is a front elevation view of the microtome specimen holder clamping assembly 24 illustrated in the FIG. 1 microtome embodiment. For ease of reference, the same reference numerals are employed in FIG. 2 for the same or corresponding elements which are illustratively shown in FIG. 1.

Figure 7:
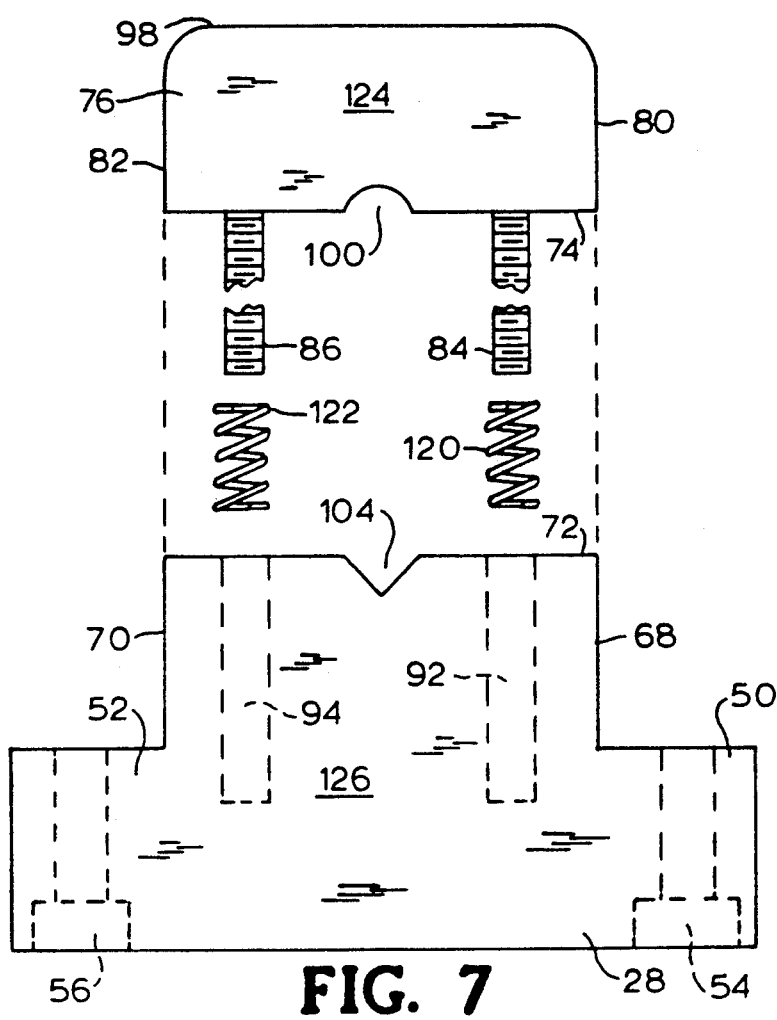
FIG. 7 is a rear elevation view of the microtome specimen holder clamping assembly whose front elevation view is shown in FIG. 3.
Figure 9:
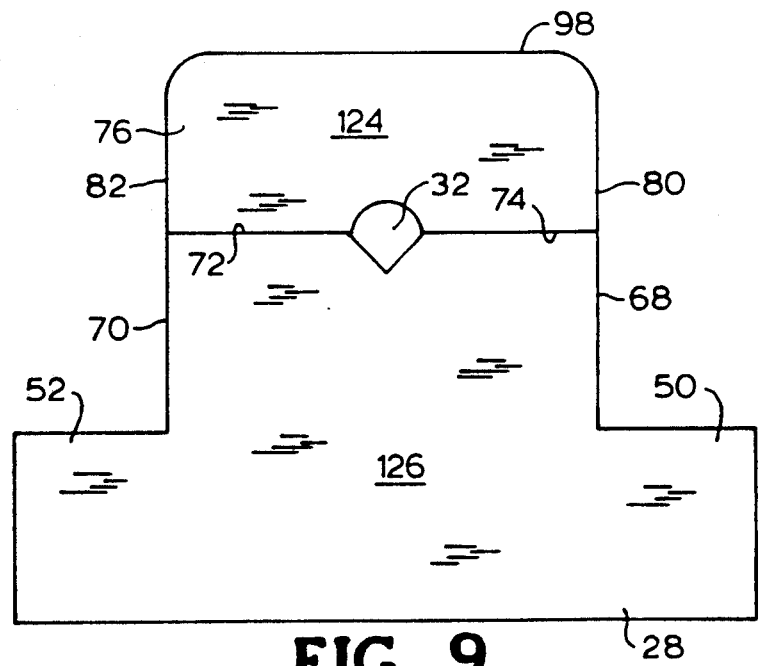
FIG. 9 is a rear elevation view of the microtome specimen holder clamping assembly shown in FIG. 5.

The specimen holder clamping assembly 24 comprises a first clamping member 28, which may be formed of steel or stainless steel with the general block-like configuration shown. The clamping member features laterally outwardly extending lower portions 50 and 52, which are bored and counterbored to provide openings 54 and 56, respectively, which accommodate insertion of the respective screw-type fasteners 58 and 60 thereinto. The upper end plate 36 is correspondingly tapped, or bored and threaded, to provide respective openings 62 and 64 receiving the distal extremities of the respective screwtype fasteners 58 and 60. The first clamping member 28 has a front main surface 66, and a corresponding back main surface (not shown in the FIG. 2 view, but as shown in FIGS. 7 and 9 hereinafter described) defining a thickness of the first clamping member therebetween. The first clamping member 28 also includes a first side surface 68 and second side surface 70, defining a width of the first clamping member therebetween.

The first clamping member 28 has a top facing surface 72 positionable in clamping proximity to a bottom facing surface 74 of the second clamping member 76. The second clamping member 76 likewise may be formed of steel or stainless steel, and has a front main surface 78 and a back main surface (not shown in FIG. 2, but as shown in FIGS. 7 and 9 hereinafter described) defining a thickness therebetween. The second clamping member also features a first side surface 80 and a second side surface 82 defining a width of the second clamping member 76 therebetween.

The first clamping member 28 is joined in adjustable vertically spaced relationship to the second clamping member 76 by means of screw-type fasteners 84 and 86 extending through the bored and counterbored passages 88 and 90 in the second clamping member 76 as shown, with the distal ends of these respective fasteners being threadably engaged with the first clamping member 28 by means of threaded openings 92 and 94, respectively.

The horizontal end plate 36 is provided with a central threaded opening 96 through which the lower threaded portion 42 of the adjustable screw member 38 is advanced or retracted as desired. This adjustable screw member is provided with a manually grippable handle 40 which may be grasped and turned in a clockwise or counterclockwise fashion to correspondingly advance or retract the lower threaded portion 42. The distal end of lower threaded portion 42 is adjustably placed in abutting relationship to the top surface 98 of the second clamping member 80.

In a medial part of the lower portion of second clamping member 76 there is provided a channel 100 which extends concavely upwardly from the bottom facing surface 74 of the second clamping member. The concave channel 100 is bounded by an arcuate surface 102 having a spherical contour, i.e., presenting a concave arcuate contour in the thickness direction of the clamping member, as well as a concave arcuate profile in the width direction of the clamping member.

Correspondingly, at a medial part of the upper portion of first clamping member 28, there is provided a channel 104 which extends convergingly downwardly from the top facing surface 72 of the first clamping member. The channel 104 is bounded by side walls 106 and 108. These side walls have a conical spherical contour. By "conical spherical contour" is meant a channel configuration in which the channel side walls define a generally V-shaped profile as shown in FIG. 2, with the side walls extending convergingly downwardly to an intersection locus defining a trough 110 extending from the main front surface to the main back surface of the first clamping member (conical aspect), while at the same time the side walls and trough have a spherical contour with a concave arcuate profile along the thickness dimension of the first clamping member, between the main front and back main surfaces thereof (spherical aspect).

As an optional feature of the invention, the main front surfaces of each of the first and second clamping members adjacent the respective channels may be champfered, to facilitate insertion and removal of the ball 44 to which the specimen plate of the object holder is attached (see FIG. 1). Thus, as shown in FIG. 2, the channel 100 of the second clamping member 76 may have a champfered surface 112. The main front surface 66 of the first clamping member 28 may likewise have a champfered surface 114 at the intersection of the main front surface with the respective side walls 106 and 108.

By means of the conical spherical contour of the channel in the first clamping member, and the spherical contour of the channel in the second clamping member, the spherical ball of a specimen holder may be retained by the clamping members when engaged in clamping proximity to one another, in abutment with the ball of the specimen holder therebetween. This provides a three point contact arrangement, wherein the specimen holder ball is contacted at a single point by the first clamping member wherein the channel contour is spherical, and at two points in the channel of the first clamping member whose side walls have a conical spherical contour.

Accordingly, by the simple expedient of threadably advancing or retracting the adjustable screw member 38, the ball of the specimen holder can readily be engaged by or disengaged from the clamping members. Preferably, as indicated, the channels of the respective clamping members are champfered to facilitate the insertion and removal of the ball of the specimen holder.

For ease of reference, the same reference numerals employed in the above-described FIGS. 1 and 2 are consistently used hereinafter with reference to the succeeding drawings FIGS. 3–21.

As shown in FIG. 2, the respective first and second clamping members 28 and 76 are joined in clamping proximity to one another by mechanical fasteners 84 and 86 (see FIG. 2), with the mechanical fasteners being circumscribed by springs 120 and 122. These springs bias the clamping members apart from one another. The adjustable screw member 38 is selectively tightenable or losenable to advance or retract the lower threaded portion 42, so that the relative spacing between the first and second clamping members is selectively increased or decreased, as desired.

FIG. 3 shows a front elevation view, and FIG. 4 the corresponding side elevation view of the first and second clamping members, wherein the respective clamping members are shown in exploded relationship to one another.

FIGS. 5 and 6 are the corresponding front and side elevation views of the first and second camping members, wherein the springs 120 and 122 have been removed from the corresponding mechanical fasteners 84 and 86, so that the second clamping member 76 is reposed against the first clamping member 28, with the respective facing surfaces 72 and 74 of these clamping members in abuttment with one another.

FIG. 6 is a partially broken away view of the side elevation of the FIG. 5 clamping assembly, wherein the portion of the assembly surrounding the cavity 32 is broken away to show the wall contours of the cavity. The cavity 32 is bounded at its upper portion by the spherical contoured wall 102 of the channel in the second clamping member 76, such channel having a champfer 112 at its frontal portion as shown. At its lower portion, the cavity 32 is bounded by the trough 10 in the channel of the first clamping member 28, such trough having a conical spherical contour. The channel in the first clamping member 28 forming the lower portion cavity 32 has a champfer 114 at its frontal part, complementary to champfer 112 of the second clamping member 76. As indicated, the champfered cavity opening at the frontal face of the first and second clamping members facilitates the insertion and removal of the ball of the ball-mounted specimen plate into and from the cavity, respectively.

Figure 8:
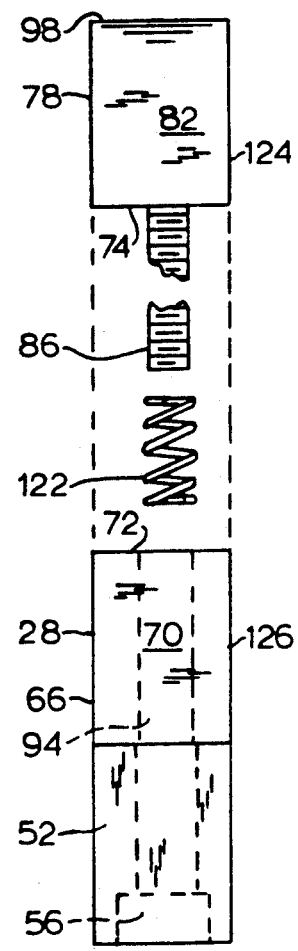
FIG. 8 is a side elevation view of the microtome specimen holder clamping, assembly of FIG. 7, showing the side of the assembly opposite to that shown in FIG. 4.

FIGS. 7 and 8 are respective rear elevation and side elevation views analogous to the front elevation and side elevation views shown in FIGS. 3 and 4, with FIG. 8 showing the opposite side of the first and second clamping members from the side shown in FIG. 4.

Figure 10:
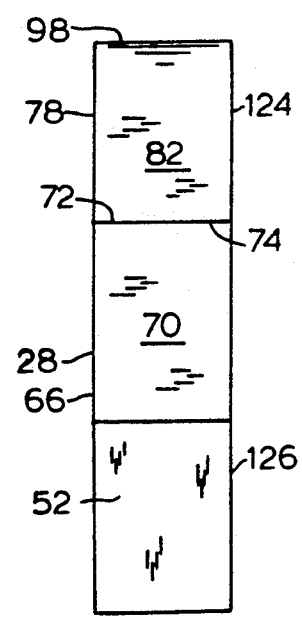
FIG. 10 is a side elevation view of the microtome specimen holder clamping assembly of FIG. 9, showing a side opposite to that of FIG. 6.

FIG. 9 and 10 are respective rear elevation and side elevation views of the first and second clamping members, mated with one another analogous to the front elevation and side elevation views of FIGS. 5 and 6, wherein the spacer springs 120 and 122 have been removed, so that the first and second clamping members are in mated abuttment with one another.

Figure 11:
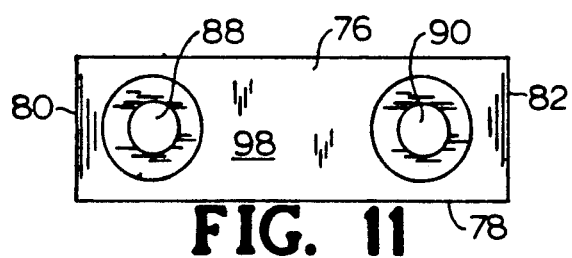
FIG. 11 is a top plan view of the first clamping member of the microtome specimen holder clamping assembly shown in the preceding drawings.
Figure 12:
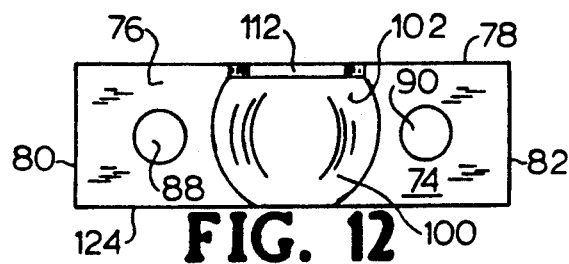
FIG. 12 is a bottom plan view of the first clamping member of FIG. 11.

FIG. 11 is a top plan view of the second clamping member 76, and FIG. 12 is the corresponding bottom plan view, each showing the provision of openings 88 and 90 extending through the clamping member for the insertion thereinto of mechanical fasteners 84 and 86. The bottom plan view of FIG. 12 also shows the spherical contour of the bounding wall 102 of channel 100

Figure 13:
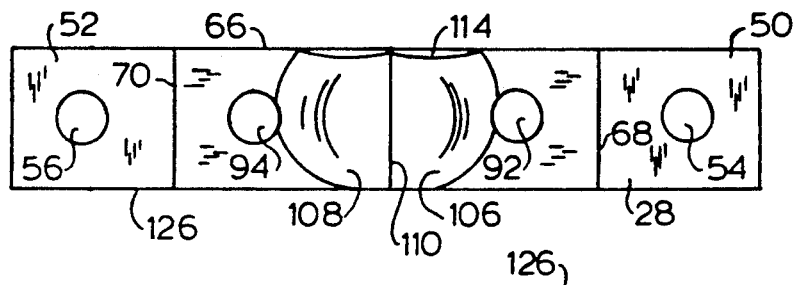
FIG. 13 is a top plan view of the second clamping member of the microtome specimen holder clamping assembly shown in the preceding drawings.
Figure 14:
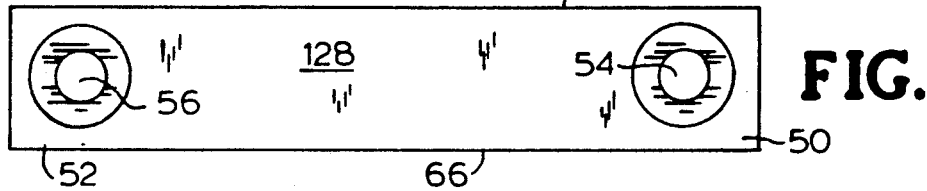
FIG. 14 is a bottom plan view of the second clamping member of FIG. 13.

FIG. 13 is a top plan view, and FIG. 14 the corresponding bottom plan view, of the first clamping member 28, showing the provision of openings 54 and 56 for insertion therethrough of mechanical fasteners 58 and 60, as shown in FIG. 2. FIG. 13 also shows the details of the generally V-shaped channel 104, which is bounded by the side walls 106 and 108 each having a conical spherical contour, with the channel side walls extending convergingly downwardly to an intersection locus defining trough 110. The trough extends from the front surface of the clamping member to the rear surface thereof as shown, and has an arcuate concave profile between the front and rear walls, when viewed in side elevation, as shown in the breakaway view of FIG. 6.

The channel 100 may be formed in the second clamping member 76 in any suitable manner, such as for example, via casting, molding, etc., of this clamping member, depending on its material of construction, which may for example comprise metals, plastics, ceramics, composites, and the like. In general, however, it is preferred to provide the clamping member with such spherically contoured channel by ball nose end milling of the block employed as the second clamping member, or by analogous machining technique.

The first clamping member, having a generally V-shaped channel with conical spherical contoured side walls and trough, can likewise be formed by casting or molding techniques. In contrast to the channel configuration of the second clamping member, however, the conical spherical contour of the channel in the first clamping member is not conveniently at economically provided by conventional mechanical milling techniques. End milling, the method normally used for mechanical milling of grooves, depressions, and the like, would cut out material which is structurally required for the conical spherical contour of the channel.

Accordingly, when machining techniques are to be employed to form the V-shaped channel of the first clamping member, electrical discharge machining is suitably employed. Such machining employs a "reverse image" electrode formed of a suitable material such as graphite, copper, copper-tungsten, or the like. The electrical discharge electrode is placed in contact with the metal block to be machined to form the first clamping member. The requisite voltage is applied to produce electrical discharge arcing and erosion of the metal, to form the reverse image of the electrode profile in the resultingly machined metal block.

Thus, discharge electrodes may be suitably formed with a reverse image of the spherical conical contour desired for the side walls and trough of the first clamping member, with the electrode being employed to "burn-in" the V-shaped channel characterized by the desired contour profiles.

In use, the clamping assembly is assembled from the constituent first and second clamping members, with the mechanical fasteners 84 and 86 (see FIG. 2) being passed through the respective openings 88 and 90 in the second clamping member, followed by mounting of respective springs 120 and 122 thereon. The second clamping member then is proximally mated with the first clamping member, by threading engagement of the distal ends of the mechanical fasteners 84 and 86 with the respective threaded openings 92 and 94 (see FIG. 13) in the first clamping member.

Figure 15:
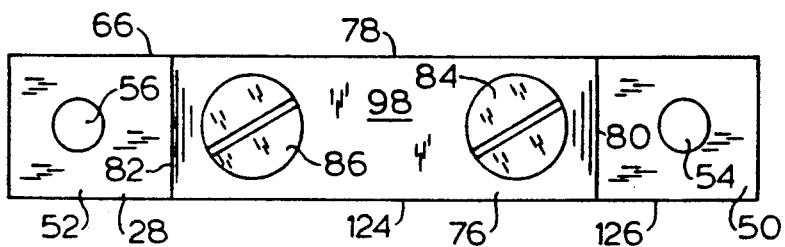
FIG. 15 is a top plan view of the abuttingly mated first and second clamping members, the frontal and rear elevation views of which are shown in FIGS. 5 and 9, respectively.

Subsequent to assembling the first and second clamping members as described in the preceding paragraph, to yield the clamping assembly which is shown in top plan view in FIG. 15, mechanical fasteners 58 and 60 are passed through the respective openings 54 and 56 in the first clamping member and then engaged at their distal ends with the respective threaded openings 62 and 64 in the horizontal end plate 36, as shown in FIG. 2.

Figure 16:
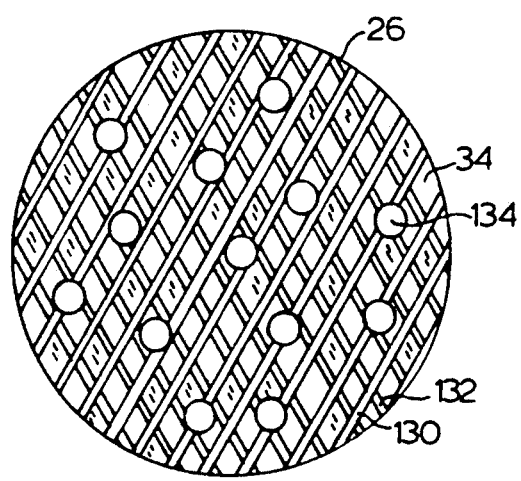
FIG. 16 is a front elevation view of a ball-mounted specimen plate use fully employed with the microtome specimen holder clamping assembly of the present invention.
Figure 17:
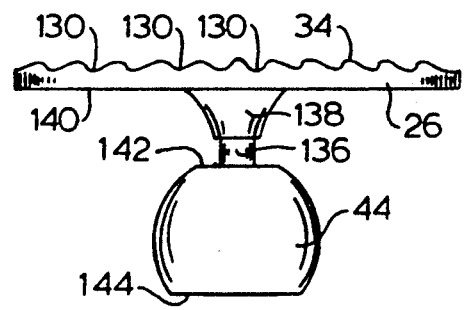
FIG. 17 is a side elevation view of the ball-mounted specimen plate of FIG. 16.
Figure 18:
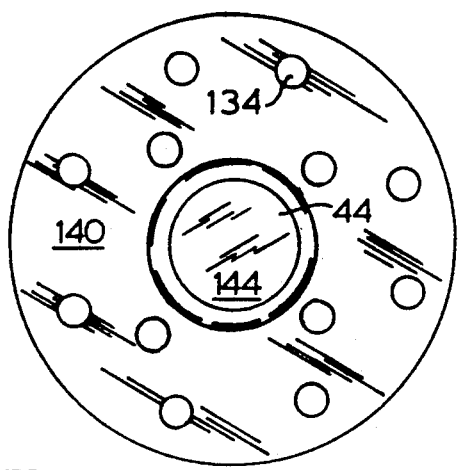
FIG. 18 is a rear elevation view of the ball-mounted specimen plate shown in FIGS. 16 and 17.

FIG. 16 shows the front face of a ball-mounted specimen plate 26, which is shown in side elevation view in FIG. 17, and with the reverse side being illustrated in FIG. 18.

The ball-mounted specimen plate 26 comprises a front surface 34 on which is provided a series of diagonally intersecting grooves 130 and 132. The intersecting grooves facilitate mounting of a selected specimen on the front face 34 of the specimen plate 26 by means of a suitable adhesive medium for embedding the specimen. To further enhance adhesion, the specimen plate 26 features an array of holes 134 extending therethrough, into which the embedding medium may spread and thereby "anchor" the embedded specimen.

As shown in the side elevational view of FIG. 17, the rear surface 140 of the specimen plate 26 has centrally joined thereto an attachment hub 138. The hub in turn is joined to the stem 136 of the ball 44. The rear face 144 of the ball as shown in FIG. 17 has been ground flat, so that such face is generally parallel to the plane of the specimen plate 26. The provision of flat face 144 may be advantageous to enable proper clearance of the ball in the microtome when the ball is positioned in the cavity 32 defined by the clamping members (see FIG. 1). In the broad practice of the invention, it may be suitable to employ a ball of substantially full spherical shape for mounting in the cavity defined by the proximately positioned first and second clamping members, depending on the structural characteristics of the microtome in which the specimen holder clamping assembly of the present invention is employed. The provision of a flat face 144 on the ball has the further advantage that it enables the ball-mounted specimen plate to be stacked on a flat surface, such as a shelf in the cooling enclosure of a cryostat microtome.

The ball 44 may suitably be formed integrally with the stem 136, or alternatively the ball element 44 may be separately formed and then machined to yield an upper planar surface 142 for attachment of the stem 136 thereto.

The ball 44 may be formed of any suitable material of construction. For example, it may be desirable in some applications to form the ball from a relatively soft and/or deformable material, and to utilize clamping members whose contact surfaces with the ball function to deform or crush the ball element to facilitate retention of the ball-mounted specimen plate in the clamping assembly. Such construction may be employed for a disposable specimen holder which is formed of low cost thermoplastic or other suitable material of construction.

Further, it is within the purview of the present invention to provide a disposable specimen holder comprising a ball which is deformable or crushable in contact with clamping members featuring metal teeth or other contacting surface structure, e.g., textured or abraded surfaces, for enhancing the gripping contact of the clamping members on the ball of the specimen holder. It is also within the purview of the present invention to provide one or more of the contacting surfaces of the ball and respective clamping members with textured, abraded, toothed, or other surface structure serving to enhance the grippability of the ball of the specimen holder by the clamping members.

FIG. 18 is a rear elevation view of the ball-mounted specimen holder, showing the central arrangement of the ball 44 relative to the rear surface 140 of the specimen plate.

Figure 19:
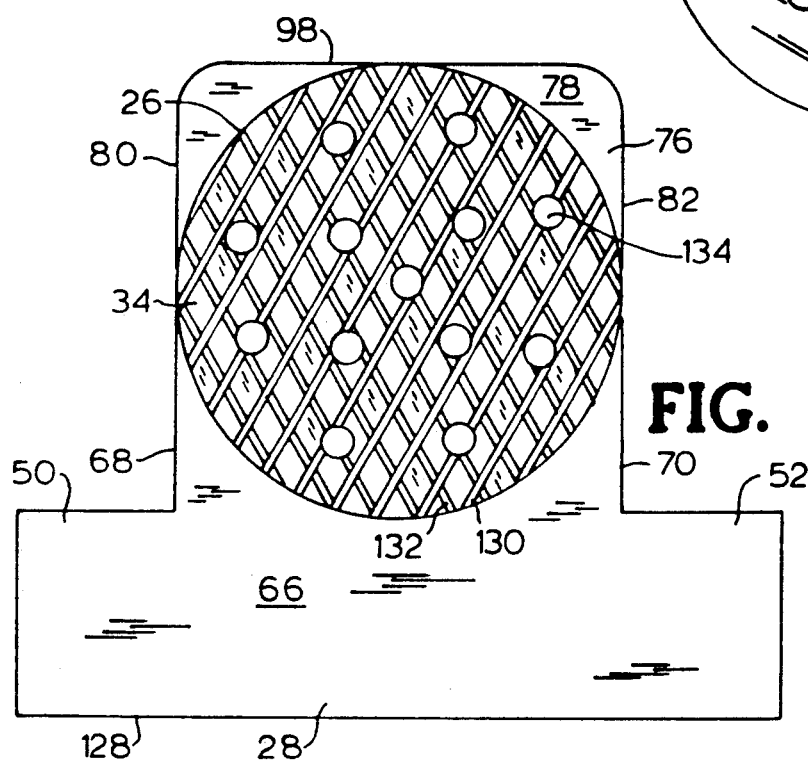
FIG. 19 is a front elevation view of a microtome specimen holder unit according to one embodiment of the present invention.

FIG. 19 is a front elevation view of the bal-mounted specimen plate 26 mounted in the clamping assembly comprising the first and second clamping members 28 and 76.

Figure 20:
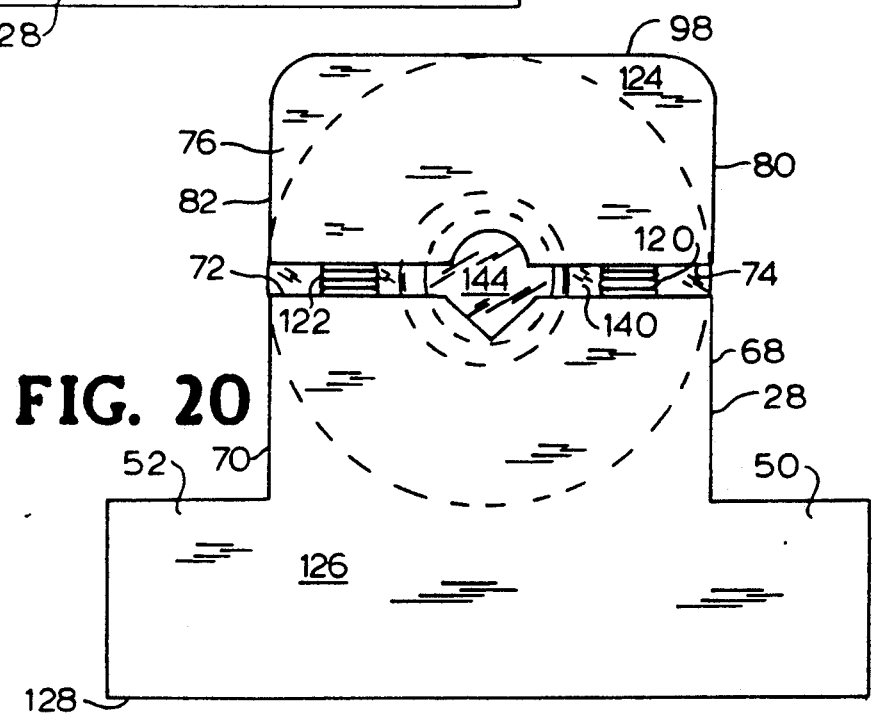
FIG. 20 is a rear elevation view of the microtome specimen holder unit of FIG. 19.

FIG. 20 is the corresponding rear elevation view of the structure shown in FIG. 19, comprising the ball-mounted specimen plate 26, wherein the ball 44 is positioned in the cavity. Concurrently, the first and second clamping members are disposed in closely adjacent relationship to one another, with the respective biasing springs 120 and 122 being compressed to provide an appropriate spacing dimension between the respective clamping members, with the ball 44 fixedly clamped therebetween.

FIG. 21 is a corresponding side elevation view of the clamping assembly of FIGS. 19 and 20, showing the first and second clamping members disposed in clamping relationship to the ball 44 of the specimen holder 34.

The clamping members of the present invention, including a first clamping member with a generally V-shaped channel therein whose side walls have a conical spherical contour, and a second clamping member with a channel bounded by an interior wall portion with a spherical contour, provides a three-point contacting of the clamping members with the ball of the ball-mounted specimen plate.

By such arrangement, with the provision of a means for selectively clampingly engaging the clamping members with the ball mounted on the specimen plate, the present invention permits a specimen-bearing plate to be clamped in a spatially fixed manner resisting pivotal or translational movement during the specimen sectioning operation.

At the same time, upon disengagement of the first and second clamping members from clamping engagement with the ball of the specimen holder, the specimen holder may be readily pivotally and/or rotationally translated, to assume any desired orientation relative to the knife of the microtome in which the object holder and associated support structure of the invention are employed.

Although the first and second clamping members have illustratively been described hereinabove as being constructed of steel or stainless steel, it will be appreciated that such members, as well as the ball-mounted specimen plate and other elements of the invention, may be formed of any of a variety of suitable materials of construction, such as for example: copper, brass, or other metals or alloys; composite materials, such as fiber reinforced epoxy or polyimide matrix materials; plastics; ceramics; etc.

It will be appreciated that although a screw-type spring-biased clamping structure has been illustratively described, any of various other structural arrangements may be employed for selectively engaging and disengaging the first and second clamping members relative to the ball element in the overall specimen holder clamping assembly. As used herein, the term "ball" is intended to be broadly construed to include any generally spherical or frustospherical element retentively engageable with the clamping members of the invention in a three-point contact mode of engagement.

Thus, while the invention has been illustratively described with reference to preferred features and embodiments thereof, it will be appreciated that various other variations, modifications, and embodiments are possible within the broad of the invention, as may be readily employed by those of ordinary skill in the art.

What is claimed is:

1. A microtome specimen holder clamping assembly for a ball-mounted specimen plate, said clamping assembly comprising:
    (a) a first clamping member, with main front and back surfaces defining a thickness of said clamping member therebetween, main first and second side surfaces defining a width of said clamping member therebetween, and a top facing surface disposable in proximate facing relationship to a second clamping member, said first clamping member having an upper portion with a generally V-shaped channel therein of thickness coextensive with the thickness of the first clamping member, with an open upper end of the channel at the top facing surface of the clamping member and conical spherical contoured side walls extending convergingly downwardly therefrom to an intersection locus defining a trough extending from said main front surface to said main back surface with an arcuate concave profile therebetween;
    (b) a second clamping member with main front and back surfaces defining a thickness of said second clamping member therebetween, main first and second side surfaces defining a width of said second clamping member therebetween, and a bottom facing surface disposable in proximate facing relationship to the top facing surface of the first clamping member, the second clamping member having a lower portion with a channel therein, with an open lower end of the second clamping member channel at said bottom facing surface, wherein the channel in the second clamping member is bounded by an interior surface having a spherical contour and defining arcuate peripheries of the channel at the respective main front and back surfaces of the second clamping member; and
    (c) means for selectively engaging the first and second clamping members in proximal clamping relationship to one another, and for selectively disengaging the first and second clamping members from said proximal clamping relationship.

2. A microtome specimen holder clamping assembly according to claim 1, wherein said means for selectively engaging and disengaging said first and second clamping members comprise mechanical fasteners joining said first and second clamping members, each of said mechanical fasteners being fixedly secured at a first end thereof to one of the first and second clamping members, with springs mounted on the respective mechanical fasteners urging the first and second clamping members away from one another.

3. A microtome holder clamping assembly according to claim 2, wherein said means for selectively engaging and disengaging said first and second clamping members further comprise a selective adjustment member for abuttingly bearing on one of the first and second clamping members, said selective adjustment member being selectively actuatable to increase or decrease spacing distance between said facing surfaces of the first and second clamping members.

4. A microtome specimen holder assembly comprising a microtome specimen holder clamping assembly according to claim 1, and a ball-mounted specimen plate including a ball of a size accommodating clamping thereof between the first and second clamping members, with spherical surface portions of the ball engaging the side walls of the generally V-shaped channel of the first clamping member and the bounding interior surface of the channel of the second clamping member.

5. A microtome comprising a microtome specimen holder clamping assembly wherein said clamping assembly comprises:
    (a) a first clamping member, with main front and back surfaces defining a thickness of said clamping member therebetween, main first and second side surfaces defining a width of said clamping member therebetween, and a top facing surface disposable in proximate facing relationship to a second clamping member, said first clamping member having an upper portion with a generally V-shaped channel therein of thickness coextensive with the thickness of the first clamping member, with an open upper end of the channel at the top facing surface of the clamping member and conical spherical contoured side walls extending convergingly downwardly therefrom to an intersection locus defining a trough extending from said main front surface to said main back surface with an arcuate concave profile therebetween;

(b) a second clamping member with main front and back surfaces defining a thickness of said second clamping member therebetween, main first and second side surfaces defining a width of said second clamping member therebetween, and a bottom facing surface disposable in proximate facing relationship to the top facing surface of the first clamping member, the second clamping member having a lower portion with a channel therein, with an open lower end of the second clamping member channel at said bottom facing surface, wherein the channel in the second clamping member is bounded by an interior surface having a spherical contour and defining arcuate peripheries of the channel at the respective main front and back surfaces of the second clamping member; and (c) means for selectively engaging the first and second clamping members in proximal clamping relationship to one another, and for selectively disengaging the first and second clamping members from said proximal clamping relationship.

6. A microtome comprising a microtome specimen holder assembly according to claim 5, further comprising a ball-mounted specimen plate including a ball of a size accommodating clamping thereof between the first and second clamping members, with spherical surface portions of the ball engaging the side walls of the generally V-shaped channel of the first clamping member and the bounding interior surface of the channel of the second clamping member.

7. A microtome comprising a microtome specimen holder clamping assembly according to claim 5 wherein said microtome comprises a cryostat microtome.

8. A microtome specimen holder clamping assembly according to claim 1, wherein the channels of the first and second clamping members are champfered at the main front surface of the clamping members.

9. A microtome specimen holder clamping assembly, comprising first and second clamping members for three point contact clamping of a ball of a ball-mounted specimen holder therebetween, wherein one of said clamping members has a generally V-shaped channel therein for two point contact with a said ball, said channel having side walls having a conical spherical contour, and the other of said clamping members has a channel therein bounded by an interior spherical contoured surface for single point contact with a said ball, and means for positioning the clamping members in a channel-facing relationship to one another and selectively varying the spacing there between.

10. A microtome specimen holder assembly according to claim 4, wherein the ball-mounted specimen plate is formed of a plastic material of construction.

11. A microtome specimen holder assembly according to claim 4, wherein at least one of the contact surfaces defined by clamping of the ball of the ball-mounted specimen plate between the clamping members comprises a contact surface structure for enhanced gripping of the ball by the clamping members.

12. A microtome specimen holder assembly according to claim 11, wherein the contact surface structure comprises a textured surface.

13. A microtome specimen holder assembly according to claim 11, wherein the contact surface structure comprises an abraded surface.

14. A microtome specimen holder assembly according to claim 4, wherein the ball is formed of a crushable material which is grippingly deformed by the clamping members upon clamping of the ball of the ball-mounted specimen plate therebetween.

15. A microtome specimen holder assembly according to claim 14, wherein the ball is formed of a thermoplastic or rubber material of construction.

* * * * *

UNITED STATES PATENT AND TRADEMARK OFFICE
CERTIFICATE OF CORRECTION

PATENT NO. : 5,082,254
DATED : January 21, 1992
INVENTOR(S) : Jack E. Hunnell, et al.

It is certified that error appears in the above-identified patent and that said Letters Patent is hereby corrected as shown below:

Column 7, line 65, change "camping" to read --clamping--.

Column 9, line 5, change "at" to read --or--.

Column 10, line 47, change "bal-mounted" to read --ball-mounted--.

Signed and Sealed this

Twentieth Day of July, 1993

Attest:

MICHAEL K. KIRK

Attesting Officer

Acting Commissioner of Patents and Trademarks